United States Patent
Shi et al.

(10) Patent No.: US 11,998,353 B2
(45) Date of Patent: Jun. 4, 2024

(54) CAMERA HAVING TRANSDERMAL OPTICAL IMAGING FUNCTION

(71) Applicant: HANGZHOU ZEMINGRUI EQUITY INVESTMENT CO., LTD., Hangzhou (CN)

(72) Inventors: Xugang Shi, Hangzhou (CN); Enrui Shi, Hangzhou (CN)

(73) Assignee: HANGZHOU ZEMINGRUI EQUITY INVESTMENT CO., LTD., Hangzhou (CN)

( * ) Notice: Subject to any disclaimer, the term of this patent is extended or adjusted under 35 U.S.C. 154(b) by 433 days.

(21) Appl. No.: 17/390,439

(22) Filed: Jul. 30, 2021

(65) Prior Publication Data

US 2021/0353220 A1   Nov. 18, 2021

Related U.S. Application Data

(63) Continuation of application No. PCT/CN2019/105487, filed on Sep. 12, 2019.

(30) Foreign Application Priority Data

Aug. 7, 2019   (CN) .......................... 201910725172.8

(51) Int. Cl.
*H04N 23/55*   (2023.01)
*A61B 5/00*   (2006.01)
(Continued)

(52) U.S. Cl.
CPC .............. *A61B 5/489* (2013.01); *A61B 5/004* (2013.01); *G06V 10/56* (2022.01); *G06V 10/751* (2022.01);
(Continued)

(58) Field of Classification Search
None
See application file for complete search history.

(56) References Cited

U.S. PATENT DOCUMENTS

| | | | |
|---|---|---|---|
| 2005/0169509 | A1 | 8/2005 | Grasslin et al. |
| 2015/0080653 | A1 | 3/2015 | Terakawa |

(Continued)

FOREIGN PATENT DOCUMENTS

| | | | |
|---|---|---|---|
| CN | 101743565 A | 6/2010 | |
| CN | 103126654 A | 6/2013 | |

(Continued)

OTHER PUBLICATIONS

Chinese Application No. 201910725172.8, First Office Action (with English translation), 13 pgs.

(Continued)

*Primary Examiner* — Samira Monshi
(74) *Attorney, Agent, or Firm* — Schwegman Lundberg & Woessner, P.A.

(57) ABSTRACT

A camera having blood optical imaging function, comprising: a lens, an image sensor, a main control module, a blood optical imaging algorithm module and an IP network interface module; the lens is located at the image acquiring position of the camera; the output end of the image sensor are in electric connection with input ends of the main control module and the blood optical imaging algorithm module, respectively; the main control module is in electric connection with the blood optical imaging algorithm module and the IP network interface module, respectively. The blood optical imaging algorithm is directly applied to the camera, so that the algorithm module can directly acquire original RGB data from the sensor, improving the accuracy of detection and the quality of blood vessel imaging, and achieving remote detection of the blood optical images of a (Continued)

face, while detecting the blood optical images of a moving face.

8 Claims, 1 Drawing Sheet

(51) Int. Cl.
    *G06V 10/56*     (2022.01)
    *G06V 10/75*     (2022.01)
    *G06V 40/10*     (2022.01)
    *H04N 25/534*     (2023.01)
    *G06V 40/14*     (2022.01)

(52) U.S. Cl.
    CPC ............. *G06V 40/10* (2022.01); *H04N 23/55* (2023.01); *H04N 25/534* (2023.01); *G06V 40/14* (2022.01)

(56) References Cited

U.S. PATENT DOCUMENTS

| | | |
|---|---|---|
| 2017/0109880 A1 | 4/2017 | Al-Kofahl et al. |
| 2019/0095681 A1* | 3/2019 | Lee ................. G06V 40/172 |

FOREIGN PATENT DOCUMENTS

| | | |
|---|---|---|
| CN | 104138254 A | 11/2014 |
| CN | 104665767 A | 6/2015 |
| CN | 105430352 A | 3/2016 |
| CN | 106073729 A | 11/2016 |
| CN | 106355575 A | 1/2017 |
| CN | 206080493 U | 4/2017 |
| CN | 107358220 A | 11/2017 |
| CN | 108471967 A | 8/2018 |
| JP | 2000033074 A | 2/2000 |
| JP | 2018171177 A | 11/2018 |
| WO | WO-2021022623 A1 | 2/2021 |

OTHER PUBLICATIONS

Chinese Application No. 201910725172.8, Second Office Action (with English translation), 16 pgs.
Chinese Application No. 201910725172.8, First Search Report, 2 pgs.
Chinese Application No. 201910725172.8, Supplemental Search Report, 2 pgs.
International Application No. PCT/CN2019/105487, International Search Report and Written Opinion dated May 7, 20, (May 7, 2020), 8 pgs.

* cited by examiner

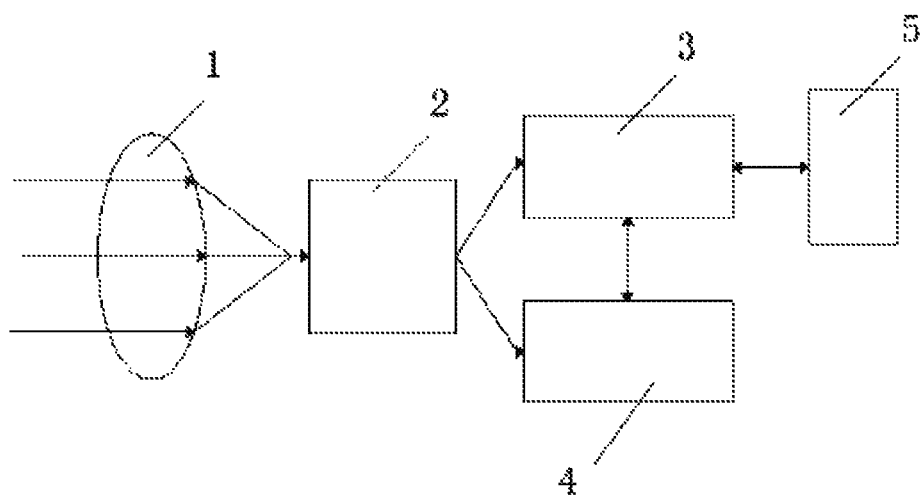

CAMERA HAVING TRANSDERMAL OPTICAL IMAGING FUNCTION

CROSS REFERENCE TO RELATED APPLICATIONS

This application is a continuation of PCT/CN2019/105487 filed 2019 Sep. 12, which claims priority to CN 201910725172.8 filed 2019 Aug. 7, both of which are incorporated herein by reference.

BACKGROUND

Field of the Invention

This invention relates to the technical field of detecting subcutaneous vessel images, and more particularly, to a camera having blood optical imaging function.

Description of the Related Art

A subcutaneous vessel image has extensive application value, for example, being applicable to the diagnosis of a medical disease, or being used for identity recognition as a biological characteristics. The human skin has the characteristics of semitransparency. When visible light irradiates on the skin, the hemoglobin in the subcutaneous vessels will absorb some of the light rays, and thus, when the blood volume in the vessels changes, the intensity of light rays as absorbed will change correspondingly, causing a corresponding change to the intensity of light rays reflected by the skin. Therefore, the optical imaging images of the skin contains the image information of subcutaneous vessels, so that the imaging of the subcutaneous vessel images has to be performed by using a special camera.

Traditional blood vessel detection algorithms are mostly obtained by a post processing of the images output by a camera, in which only the areas of interest can be processed to obtain a profile showing the blood change in the whole area. However, such a method requires an extremely high quality of the original images, and can not provide a complete dynamic image of fine vessels. If the images output by the camera are used, for example, virtual video or IP video, large amount of the detail information of the pixels will be lost due to the digitization or compression/decompression processing of the video output by the camera, so that it is difficult to extract the dynamic images of the blood vessels, which in turn leads to insufficient imaging accuracy of the subcutaneous vessel images.

BRIEF SUMMARY

The objection of the present application is to provide a camera having blood optical imaging function, for the purpose of addressing the defects present in the prior art.

In order to achieve the above object, the present application adopts the following technical solution: a camera having blood optical imaging function, comprising: a lens, an image sensor, a main control module, a blood optical imaging algorithm module and an IP network interface module;

The lens is located at the image acquiring position of the camera;

the output end of the image sensor is in electric connection with the input ends of the main control module and the blood optical imaging algorithm module, respectively;

the main control module is in electric connection with the blood optical imaging algorithm module and the IP network interface module, respectively.

As a further implementation of the above technical solution:

the lens is an optical lens, wherein the optical lens is used to focus an optical image onto the image sensing module of the image sensor to obtain a complete and clear optical image.

As a further implementation of the above technical solution:

the image sensor is a CCD or CMOS sensor, wherein the image sensing module of the image sensor is used to output original RGB signals into the main control module and the blood optical imaging algorithm module, so as to obtain accurate original RGB signals.

As a further implementation of the above technical solution:

the main control module adopts an AI chip, wherein the main control module is used for controlling the image sensor and the lens. The main control module can be of Model 3519A Hisilicon AI Chip, or can be other AI chips having similar functions.

As a further implementation of the above technical solution:

the controlling of the image sensor and the lens by the main control module comprises exposure control, automatic white balance control, and lens aperture control, which ensures that the image sensor and the lens can acquire the best image signals.

As a further implementation of the above technical solution:

The main control module can further compression encode the original images and package the same into IP signal packets after the compression encoding, wherein the formats for compression encoding comprises H.265, H.264, MPEG2, MPEG4, or MJPEG.

As a further implementation of the above technical solution:

the blood optical imaging algorithm module is used for extracting continuously changed dynamic optical images of the face blood vessels from the RGB digital image signals, and send the same into the main control module for packaging into IP data packets, ensuring a full extraction of the images.

As a further implementation of the above technical solution:

the calculation method of the blood optical imaging algorithm module comprises the following steps:

S01: continuously reading the data of N frames of RGB image from the optical video images of the subcutaneous vessels of a living body as detected in the image sensor;

S02: selecting the green component G of the image data from the continuously read RGB image data as the original data for extracting blood optical images, in which the green component G of the image data corresponds to the green pixels of the subcutaneous areas where a blood vessel is located, from which it can be determined whether a pixel is a blood vessel pixel:

S03: calculating the change rule of the green component $G(x,y)$ of each pixel in the data of continuous N frames of images, and marking and identifying all the pixel classes in the N frames of images;

S04: performing calculation to the data of the selected N frames of images to provide numerical values, from which the blood optical imaging images directed to the data of each frame of the images, that is, the blood optical images, can be obtained.

As a further implementation of the above technical solution:

in the step S03, the values of a pixel (G component value G(x,y) of x,y) at a certain subcutaneous position of the face in the continuous N frames of images constitute a G component sequence {G(x,y)[n]} where 0≤n<N, by which the component sequences of the pixels at all subcutaneous positions of the face can be calculated.

As a further implementation of the above technical solution:

the G component sequence {G(x,y)[n]} where 0≤n<N is subject to DFT transformation to provide a frequency spectrum Fx,y[k] of the pixel, from which it can be determined whether the pixel has the same change rule as that of the heartbeat.

Beneficial Effect

The present application provides a camera having blood optical imaging function, which has the following beneficial effects:

(1) the camera directly adopts a blood optical imaging algorithm, so that the algorithm module can acquire original RGB data directly from the sensor provided in the camera, and thus can greatly improve the accuracy of detection and the quality of blood vessel imaging.

(2) since the camera acquires RGB data directly from the image sensor, these data can record fine changes of the pixels corresponding to the positions of blood vessels to the utmost, ensuring that the camera can remotely detect the blood optical images of a face while being capable of detecting the blood optical images of a moving face.

BRIEF DESCRIPTION OF THE DRAWINGS

FIG. 1 is a schematic view of the overall structure of a camera having blood optical imaging function according to one embodiment of the present application.

The reference numerals in the drawings are as follow:
1. lens; 2. image sensor; 3. main control module: 4. blood optical imaging algorithm module; 5. IP network interface module.

DETAILED DESCRIPTION

The technical solutions in the embodiments of the present application will be clearly and completely described below in connection with the drawings according to the embodiments of the present application. It is apparent that the embodiments as described are only part, but not all, of the embodiments of the present application.

As shown in FIG. 1, a camera having blood optical imaging function comprises: a lens 1, an image sensor 2, a main control module 3, a blood optical imaging algorithm module 4, and an IP network interface module 5.

The lens 1 is located at the image acquiring position of the camera;

the output end of the image sensor 2 are in electric connection with the input ends of the main control module 3 and the blood optical imaging algorithm module 4, respectively;

the main control module 3 is in electric connection with the blood optical imaging algorithm module 4 and the IP network interface module 5, respectively.

The lens 1 is an optical lens. In particular, the optical lens is used to focus an optical image onto the image sensing module of the image sensor 2 to obtain a complete and clear optical image.

The camera can adopt a manually controlled lens or automatically controlled lens: a lens having standard definition or a high definition lens; a virtual camera or an IP camera; a gun camera or a hemispherical camera; or various cameras having PTZ control function, such as a spherical camera or a cloud camera, as long as the blood optical imaging algorithm module 4 can be mounted therein so that the blood flow information of the subcutaneous vessels of the face can be continuously imaged and acquired in real time manner.

The image sensor 2 is a CCD or CMOS sensor. Preferably, the image sensor 2 adopts an IMX385 CMOS digital image sensor. In particular, the image sensing module of the image sensor 2 is used to output original RGB signals into the main control module 3 and the blood optical imaging algorithm module 4, so as to obtain accurate original RGB signals.

The main control module 3 adopts an AI chip. In particular, the main control module 3 is used for controlling the image sensor and the lens. The main control module 3 can be of Model 3519A Hisilicon AI Chip, or can be another AI chip having similar functions.

The IP network interface module 5 adopts a normal network interface chip to complete the connection with electric port/optical port 10M/100M/1000M Ethernet, so as to transmit IP data packets into the network via RJ45/optical port.

The controlling of the image sensor 2 and the lens 1 by the main control module 3 comprises exposure control, automatic white balance control, and lens aperture control, which ensures that the image sensor 2 and the lens 1 can acquire the best image signals.

The main control module 3 can further compression encode the original images and package the same into IP signal packets after the compression encoding. In particular, the formats for compression encoding comprises H.265, H.264, MPEG2, MPEG4, or MJPEG.

The blood optical imaging algorithm module 4 is used for extracting continuously changed dynamic optical images of the face blood vessels from the RGB digital image signals, and send the same into the main control module 3 for packaging into IP data packets, ensuring a full extraction of the images.

The calculation method of the blood optical imaging algorithm module 4 comprises the following steps:

S01: continuously reading the data of N frames of RGB image from the optical video images of the subcutaneous vessels of a living body as detected in the image sensor 2;

S02: selecting the green component G of the image data from the continuously read RGB image data as the original data for extracting blood optical images, in which the green component G of the image data corresponds to the green pixels of the subcutaneous areas where a blood vessel is located, from which it can be determined whether a pixel is a blood vessel pixel;

S03: calculating the change rule of the green component G(x,y) of each pixel in the data of continuous N frames of images, and marking and identifying all the pixel classes in the N frames of images;

S04: performing calculation to the data of the selected N frames of images to provide numerical values, from which the blood optical imaging images directed to the data of each frame of the images, that is, the blood optical images, can be obtained.

In the step S03, the values of a pixel (G component value G(x,y) of x,y) at a certain subcutaneous position of the face in the continuous N frames of images constitute a G component sequence {G(x,y)[n]} where $0 \leq n < N$, by which the component sequences of the pixels at all subcutaneous positions of the face can be calculated.

The G component sequence {G(x,y)[n]} where $0 \leq n < N$ is subject to DFT transformation to provide a frequency spectrum Fx,y[k] of the pixel, from which it can be determined whether the pixel has the same change rule as that of the heartbeat.

In describing the present disclosure, the description made by referring to the terms "one embodiment", "example", "particular embodiment" means that the particular features, structures, material or characteristics described in connection with embodiments or examples are included in at least one embodiment or example of the present application. In this disclosure, the exemplified expression of the above terms does not necessarily refer to the same embodiment or example. Furthermore, the particular feature, structure, material or characteristics as described can be appropriately combined with each other in any one or more of embodiments or examples.

What are described above are merely preferred embodiments of the present application, and the scope of the present application is not limited thereto. Equivalent alternative or changes within the scope disclosed by the present application made by those skilled in the art according to the technical solutions and the concepts thereof shall be included in the scope of the present application.

What is claimed is:

1. A camera having blood optical imaging function, comprising:
    a lens (1), an image sensor (2), a main control module (3), a blood optical imaging algorithm module (4) and an IP network interface module (5);
    the lens (1) is located at an image acquiring position of the camera;
    an output end of the image sensor (2) are in electric connection with input ends of the main control module (3) and the blood optical imaging algorithm module (4), respectively;
    the main control module (3) is in electric connection with the blood optical imaging algorithm module (4) and the IP network interface module (5), respectively;
    the blood optical imaging algorithm module (4) is used for extracting continuously changed dynamic optical images of the face blood vessels from the RGB digital image signals, and send the same into the main control module (3) for packaging into IP data packets, ensuring a full extraction of the images; and
    the calculation method of the blood optical imaging algorithm module (4) comprises the following steps:
    S01: continuously reading the data of N frames of RGB image from the optical video images of the subcutaneous vessels of a living body as detected in the image sensor (2);
    S02: selecting the green component G of the image data from the continuously read RGB image data as the original data for extracting blood optical images, in which the green component G of the image data corresponds to the green pixels of the subcutaneous areas where a blood vessel is located, from which it can be determined whether a pixel is a blood vessel pixel;
    S03: calculating the change rule of the green component G(x,y) of each pixel in the data of continuous N frames of images, and marking and identifying all the pixel classes in the N frames of images; and
    S04: performing calculation to the data of the selected N frames of images to provide numerical values, from which the blood optical imaging images directed to the data of each frame of the images, that is, the blood optical images, can be obtained.

2. The camera having blood optical imaging function according to claim 1, characterized in that, the lens (1) is an optical lens, wherein the optical lens is used to focus an optical image onto the image sensing module of the image sensor (2) to obtain a complete and clear optical image.

3. The camera having blood optical imaging function according to claim 1, characterized in that, the image sensor (2) is a CCD or CMOS sensor, wherein the image sensing module of the image sensor (2) is used to output original RGB signals into the main control module (3) and the blood optical imaging algorithm module (4), so as to obtain accurate original RGB signals.

4. The camera having blood optical imaging function according to claim 1, characterized in that, the main control module (3) adopts an AI chip, wherein the main control module (3) is used for controlling the image sensor (2) and the lens (1).

5. The camera having blood optical imaging function according to claim 4, characterized in that, the controlling of the image sensor (2) and the lens (1) by the main control module (3) comprises exposure control, automatic white balance control, and lens aperture control, which ensures that the image sensor (2) and the lens (1) can acquire the best image signals.

6. The camera having blood optical imaging function according to claim 1, characterized in that, the main control module (3) can further compression encode the original images and package the same into IP signal packets after the compression encoding, wherein the formats for compression encoding comprises H.265, H.264, MPEG2, MPEG4, or MJPEG.

7. The camera having blood optical imaging function according to claim 1, characterized in that, in the step S03, the values of a pixel (G component value G(x,y) of x,y) at a certain subcutaneous position of the face in the continuous N frames of images constitute a G component sequence {G(x,y)[n]} where $0 \leq n < N$, by which the component sequences of the pixels at all subcutaneous positions of the face can be calculated.

8. The camera having blood optical imaging function according to claim 7, characterized in that, the G component sequence {G(x,y)[n]} where $0 \leq n$.

* * * * *